United States Patent [19]

Foster et al.

[11] Patent Number: 5,217,954
[45] Date of Patent: Jun. 8, 1993

[54] FORMULATIONS FOR STABILIZING FIBROBLAST GROWTH FACTOR

[75] Inventors: Linda C. Foster, Sunnyvale; Stewart A. Thompson, Mountain View; S. Joseph Tarnowski, Sunnyvale, all of Calif.

[73] Assignee: Scios Nova Inc., Mountain View, Calif.

[21] Appl. No.: 504,340

[22] Filed: Apr. 4, 1990

[51] Int. Cl.$^5$ ............................................. A61K 37/36
[52] U.S. Cl. ........................................ 514/12; 514/21; 514/970; 530/399
[58] Field of Search .......................... 514/12, 970, 21; 530/399

[56] References Cited

U.S. PATENT DOCUMENTS

| | | | |
|---|---|---|---|
| 4,785,079 | 11/1988 | Gospodarowicz | 514/12 |
| 4,900,730 | 2/1990 | Miyauchi | 514/12 |
| 4,902,782 | 2/1990 | Gospodarowicz | 530/412 |

OTHER PUBLICATIONS

Bruce Alberts et al., *Molecular Biology of the Cell*, Garland Publishing Inc., N.Y. 1983, p. 212.
Bohlen et al., *Proc. Natl. Acad. Sci. USA*, 81, 5364–5368, 1984.
Thomas, *The FASEB Journal*, 1, No. 6, 434–440, 1987.
Abraham et al., (1986) *EMBO Journal* 5(10):2523–2528.
Abraham et al., (1986) *Science* 233:545–548.
Buckley et al., (1985) *Proc. Natl. Acad. Sci. USA* 82:7340–7344.
Canalis et al., (1987) *Journal of Clinical Investigation* 79:52–58.
Davidson et al., (1985) *Journal of Cell Biology* 100:1219–1227.
Fox et al., (1988) *Journal of Biological Chemistry* 263 (34):18452–18458.
Gospodarowicz et al., (1979) *Exp. Eye Res.* 28:501–514.
Gospodarowicz et al., (1981) *Advances in Neurology* 29:149–171.
Gospodarowicz et al., (1985) *Journal of Cellular Physiology* 122:323–332.
Gospodarowicz et al., (1986) *Jouranl of Cellular Physiology* 128: 475–484.
Gospodarowicz et al., (1987) *Endocrine Reviews* 8(2):95–114.
Greisler et al., (1986) *Trans. Am. Soc. Artif. Intern. Organs* 32:346–349.
Morrison et al., (1986) *Proc. Natl. Acad. Sci.* 83:7537–7541.
Moscatelli et al., (1986) *Proc. Natl. Acad. Sci.* 83:2091–2095.
Neufeld et al., (1986) *Regulatory Peptides* 13:293–332.
Presta et al., (1986) *Molecular and Cellular Biology* 6(11):4060–4066.
Senior et al., (1986) *Biochem. Biophys. Res. Commun.* 141 (1):67–72.
Wu et al., (1983) *Analytical Biochemistry* 129:345–348.
Yamada, (1982) in *Cell Biology of the Eye* (Academic Press), pp. 193–242.

*Primary Examiner*—F. T. Moezie
*Attorney, Agent, or Firm*—Morrison & Foerster

[57] ABSTRACT

Pharmaceutical formulations and a method for their preparation are provided. These formulations provide a stabilized basic fibroblast growth factor (bFGF) which is less susceptible to oxidation or metal-induced aggregation by including an amount of a chelating agent effective to stabilize the bFGF.

20 Claims, 5 Drawing Sheets

FORMULATIONS FOR STABILIZING FIBROBLAST GROWTH FACTOR

FIELD OF THE INVENTION

The invention relates generally to methods to inhibit oxidation of basic fibroblast growth factor (bFGF) and to provide stable pharmaceutical formulations thereof.

BACKGROUND OF THE INVENTION

Many proteins undergo varying degrees of modification during purification and storage. Certain proteins are known to be unusually susceptible to thermal denaturation or to proteolytic cleavage; others contain reactive amino acid side chains, which due to their location within the tertiary structure of the protein, are particularly susceptible to chemical modification, including oxidation. While the tertiary structure of the protein, if known, may suggest what forces can be used in its stabilization, it is generally not possible to predict the extent to which any of the modifications will occur.

It is also known that various metals can act as catalysts of oxidation. Due to the ease with which such products are oxidized, antioxidants are frequently required to stabilize proteins in a pharmaceutical formulation.

Basic fibroblast growth factor (bFGF) is currently undergoing clinical trials for wound healing indications. Although early preparations were shown to be biologically active through in vitro cell assay, formulations of nonreduced bFGF produced heterogeneous mixtures, and it was discovered that multimers of reduced bFGF were formed after short-term storage at room temperature, under refrigeration, or in the frozen state. In addition, more sophisticated analytical techniques such as quasi-elastic light-scattering techniques and UV spectroscopy, have revealed that insoluble aggregates can form in aged solution formulations at higher bFGF concentrations (1 mg/ml or greater) and in lyophilized formulations.

In light of these discoveries, it would be desirable to provide pharmaceutical formulations of bFGF that overcome these problems by providing compositions that improve the stability of bFGF both in solution and in lyophilized form.

DISCLOSURE OF THE INVENTION

The present invention provides a means to protect bFGF from oxidation during storage and clinical use. It has been found that the presence of certain chelating agents effectively stabilizes this protein against oxidation of its free cysteine residues or metal-induced aggregation, thereby preserving the homogeneity of the purified product. Thus protected, the resulting stabilized protein retains useful biological activity and exhibits enhanced chemical stability.

In one aspect, the invention provides a stabilized bFGF formulation and a method for its manufacture. The invention provides for the preservation of the soluble bioactivity of the FGF in an aqueous environment, or for the stabilized bioactivity in a dry environment. The FGF formulation can be formed by mixing FGF with an amount of a chelating agent effective to stabilize the FGF.

Preferred chelating agents useful in the present invention are those which have high chelating abilities as measured by their stability constants with respect to heavy metal ions, such as aminopolycarboxylic acids and hydroxyaminocarboxylic acids, and combinations thereof.

MODES OF CARRYING OUT THE INVENTION

Figure 1A:
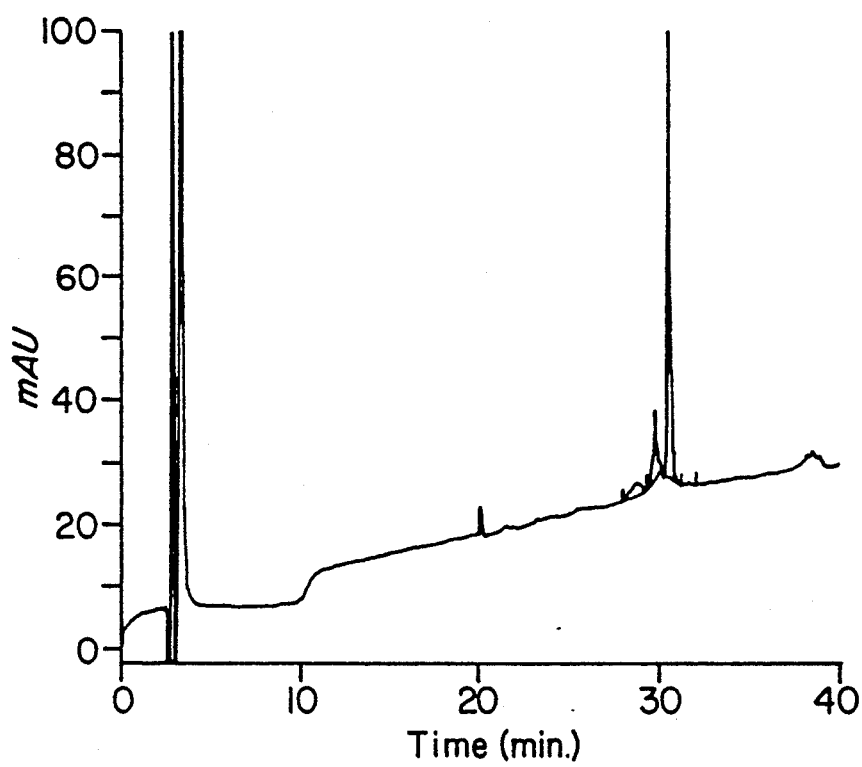
FIGS. 1A and 1B show reverse-phase HPLC chromatograms of bFGF in the presence of EDTA (FIG. 1A) and in the absence of EDTA (FIG. 1B).

Many endothelial cell mitogens of 13,000-18,000 molecular weight with a strong affinity for heparin and basic isoelectric point (pI) have been isolated from mammalian sources (see Fox et al., *J Biol Chem* (1988) 263:18452-18458 for a summary of these mitogens). As used herein the term "mammalian" refers to any mammalian species, and includes rabbits, mice, dogs, cats, primates and humans, preferably humans. It is now known that all of these factors are forms of bFGF differing only in the degree of N-terminal processing. The bFGF for use in the present invention can be derived by extraction and subsequent concentration techniques from the pituitary gland of various animals. As isolated from pituitary tissue, bFGF is a single chain, nonglycosylated protein of 16,500 molecular weight.

This growth factor can also be produced by recombinant methods as disclosed in PCT Publication WO87/01728, published Mar. 26, 1987, the relevant portions of which are incorporated herein by reference. As the DNA sequences are known for a number of mammalian-derived bFGF molecules (for example, the bovine cDNA sequence is provided in Abraham et al., *Science* (1986) 233:545 and the human cDNA sequence is disclosed in Abraham et al., *EMBO J* (1986) 5:2523-2528), a number of gene sequences may be employed for the expression of recombinant bFGF.

Briefly, these techniques involve identifying and characterizing the structural gene which encodes the native protein, isolating or synthesizing that gene or its degenerate equivalent or a gene encoding a functionally equivalent analog of the native protein, inserting the gene into an appropriate expression vector in a position which permits expression of the gene, transforming competent heterologous hosts, preferably microorganisms, with the vector, identifying correct transformants, and culturing the transformants in a suitable growth medium. The protein is typically recovered from the culture by disrupting the cells, treating the cellular debris with solubilizing agents (depending on the solubility characteristics of the protein) and one or more extractants to isolate crude protein, and purifying the crude protein by various preparative chromatography procedures. If the expression system is so constructed, the protein may also be secreted into the medium. If the protein is susceptible to oligomer formation during the fermentation or recovery processes, the protein will be treated with a reducing agent at an appropriate stage in the recovery process.

In addition to the production of native, mammalian bFGF, the term "recombinant protein" or "recombinant bFGF" as used herein also refers to analogs of bFGF. Such analogs are described in PCT publication WO88/00198, published Jan. 12, 1989, the relevant portions of which are incorporated herein by reference. These analogs include, for example, proteins in which one or more residues within designated heparin binding domains have been replaced with another amino acid to eliminate negatively charged portion of the protein, thereby reducing the analog's affinity for heparin.

After the protein is recovered from the host or from the native tissue in a substantially pure, or pure form, it is formulated with a stabilizer using the invention process. The stabilizers which are suitable for the present invention are chelating agents which are effective in inhibiting oxidative reactions or metal-induced aggregation. These agents generally operate by removing catalyzing metals, such as copper, iron, zinc, nickel, cadmium, or chromium that are ubiquitous in trace amounts. The chelating agents should be soluble in aqueous solutions to the extent necessary to provide effective stabilization. According to one embodiment, the stabilizer is preferably present in amounts sufficient such that when the stabilizer-growth factor formulation is in an aqueous environment or solution, the trace metals are completely sequestered.

The stabilizers useful in the invention are metal chelating agents generally known in the art. Chelators for metal ions are generally polyfunctional molecules which have a multiplicity of negatively charged and/or electron-rich ligands which can sequester metal ions with varying affinities. Suitable electron-rich functional groups include carboxylic acid groups, hydroxy groups and amino groups. Arrangement of these groups in aminopolycarboxylic acids, hydroxypolycarboxylic acids, hydroxyaminocarboxylic acids, and the like result in moieties which behave as excellent chelators. These include aminopolycarboxylic acids such as, for example, ethylenediaminetetraacetic acid (EDTA), diethylenetriamine pentaacetic acid (DTPA), nitrilotriacetic acid (NTA), N-2-acetamido-2-iminodiacetic acid (ADA), bis(aminoethyl)glycolether, N,N,N',N'-tetraacetic acid (EGTA), trans-diaminocyclohexane tetraacetic acid (DCTA), glutamic acid, and aspartic acid; and hydroxyaminocarboxylic acids, such as, for example, N-hydroxyethyliminodiacetic acid (HIMDA), N,N-bis-hydroxyethylglycine (bicine) and N-(trishydroxymethylmethyl)glycine (tricine); and N-substituted glycines such as glycylglycine. Other candidate chelators include 2-(2-amino-2-oxocthyl)aminoethane sulfonic acid (BES). All the foregoing also include the salts of carboxyl or other acidic functionalities.

Examples of such salts include salts formed with sodium, potassium, calcium, and other weakly bound metal ions; the nature of the salt and the number of charges to be neutralized will depend on the number of carboxyl groups present and the pH at which the stabilizing chelator is supplied.

As is understood in the art, chelating agents have varying strengths with which particular target ions are bound. In general, heavy metal ions are bound more strongly than their similarly charged lower molecular weight counterparts. For example, $Cu^{+2}$ is uniformly chelated more strongly than $Ca^{+2}$, accounting for the ability, in some instances, to use calcium salts of the chelators supplied. In order to assess relative strength, the stability constant with respect to copper ion at the pH of the formulation is used herein as an arbitrary standard for comparison of chelators. These stability constants are, of course, pH dependent. They are readily available in the literature, and can be found for example, in Perrin, D. D., et al., "Buffers for pH and Metal Ion Control" Chapman & Hall, London, N.Y., (1974), and, in particular, in International Union of Pure & Applied Chemistry: "Stability Constants", suppl 1 (1971) Alden press, Oxford. Using the values for stability of the $Cu^{+2}$ complexes found in these references as a measure of the strength of the chelator, one can set classifications of chelator strength. The "log beta" values are used—these are the negative logarithms of the dissociation constant for the complex. The higher the value of log-beta, therefore, the stronger the association between the copper ion and the chelating moiety. Of course, the pH at which determination is made is significant, since the various carboxylic acid groups contained in the chelator bind more strongly to the sequestered ion when they are negatively charged.

Particularly useful in the invention are chelators with log-beta values for copper ion (as determined at the pH of the proposed formulation) of about 7 or more; more preferred are those with values of 10 or more; and most preferred are those with log-beta values at the pH of use of 15 or more. Thus, for example, tricine, bicine, ADA and HIMDA are preferred, as these are fairly strong; even more preferred are NTA, DTPA, and EDTA. Among the most preferred chelators for use in the invention are EDTA and DTPA.

A large number of chelating agents is known in the art, and a candidate chelator can readily be evaluated by determination of its log-beta value with respect to copper ion at the intended pH of use and, provided it has pharmaceutically acceptable properties which permit its use in compositions to be administered to animal subjects, can be evaluated conveniently for use in the invention method and in the invention compositions.

Solubilities in water should also be considered, though the various chelators may be present in different amounts, depending on the nature of the remainder of the formulation.

While the concentration of the chelating agent is present in stabilizing amounts, the percent chelating agent total weight can be present in amounts of from about 0.001% to about 2.0% percent (weight/weight) of the overall formulation. Preferably, the percent chelating agent total weight is present in amounts of from about 0.04% to about 0.7% percent (weight/weight). These values refer to final reconstituted product for pharmaceutical indications. If the formulation is lyophilized, the percent chelating agent in the dry cake may be as high as about 10 to about 40%. Therefore, in dry form the chelating agent can be present in amounts of about 0.01% to about 40% total weight, preferably about 1.0% to about 30%. As one of skill in the art would recognize, the percentage of the chelating agent in the formulation varies depending upon the particular bulking agent used to formulate the active compound. Clearly, the higher the levels of problematic metal ions present in the bulking agent or otherwise in the composition, the higher the levels of chelator required. It is a simple matter, using the techniques described hereinbelow, to determine optimal concentrations of the chelating agent.

The stabilizer can be introduced in combination with other stabilizers, such as citrate, which is a nontoxic, nonvolatile buffer suitable for lyophilization use, and also providing metal chelating activity. In this embodiment, the specific amounts of each stabilizer present in the combination may be reduced in comparison to the amount present if the specific stabilizer is used singularly in the formulation. In yet another alternative formulation, the stabilizer can be added in combination with nitrogen- or argon-purged environment to reduce the amount of oxygen present in the product container.

The preparation of the formulations containing the stabilizing chelator and the bFGF may be made by simple mechanical mixing. Alternatively, the stabilizer may be introduced during the final chromatography step in the purification process, thereby eliminating the need for subsequent mixing steps. For parenteral, for example, subcutaneous or intramuscular, or topical administration, bFGF formulations are converted into a solution, gel or emulsion, if desired, using the pharmaceutical substances customary for this purpose, such as solubilizers, thickening agents, emulsifiers, agents for tonicity, preservatives or other auxiliaries. Examples of suitable solvents for the new active compounds and the corresponding physiologically tolerated salts are: water, physiological saline solutions or alcohols, for example ethanol, propanediol, glycerol, or mannitol, as well as sugar solutions, such as glucose or lactose solutions, or a mixture of the various solvents mentioned.

The topical vehicles used in pharmacy are aqueous solutions which are, for example, buffer systems or isotonic mixtures of water and solvents which are miscible with water, such as, for example, alcohols or aryl alcohols, oils, polyalkylene glycols, ethylcellulose, hydroxypropylcellulose carboxymethylcellulose, polyvinylpyrrolidone or copolymers of ethyleneoxide and propyleneoxide (pluronic) isopropylmyristate. Examples of suitable buffer substances are sodium citrate, sodium borate, sodium phosphate, sodium acetate or gluconate buffer. The topical administration form can also contain nontoxic auxiliaries such as, for example, polyethylene glycols, and antibacterial compounds.

Continuous release formulations are also contemplated within the scope of the present invention. Such formulations are of considerable variety, as will be understood by those skilled in the art. Exemplary continuous release substances include organic solvents or biodegradable, biocompatible polymers, including, for example, emulsions, gels, microspheres and hydrogels. Preferred continuous release formulations for use in conjunction with the present invention is the microcapsule or microsphere. Microcapsules/spheres are essentially small particles of active compounds embedded in a suitable polymer to form spheres ranging in diameter from about 40-500 um (preferably less than 150 um) and are easily administered by injection when suspended in a suitable liquid vehicle.

Figure 5:
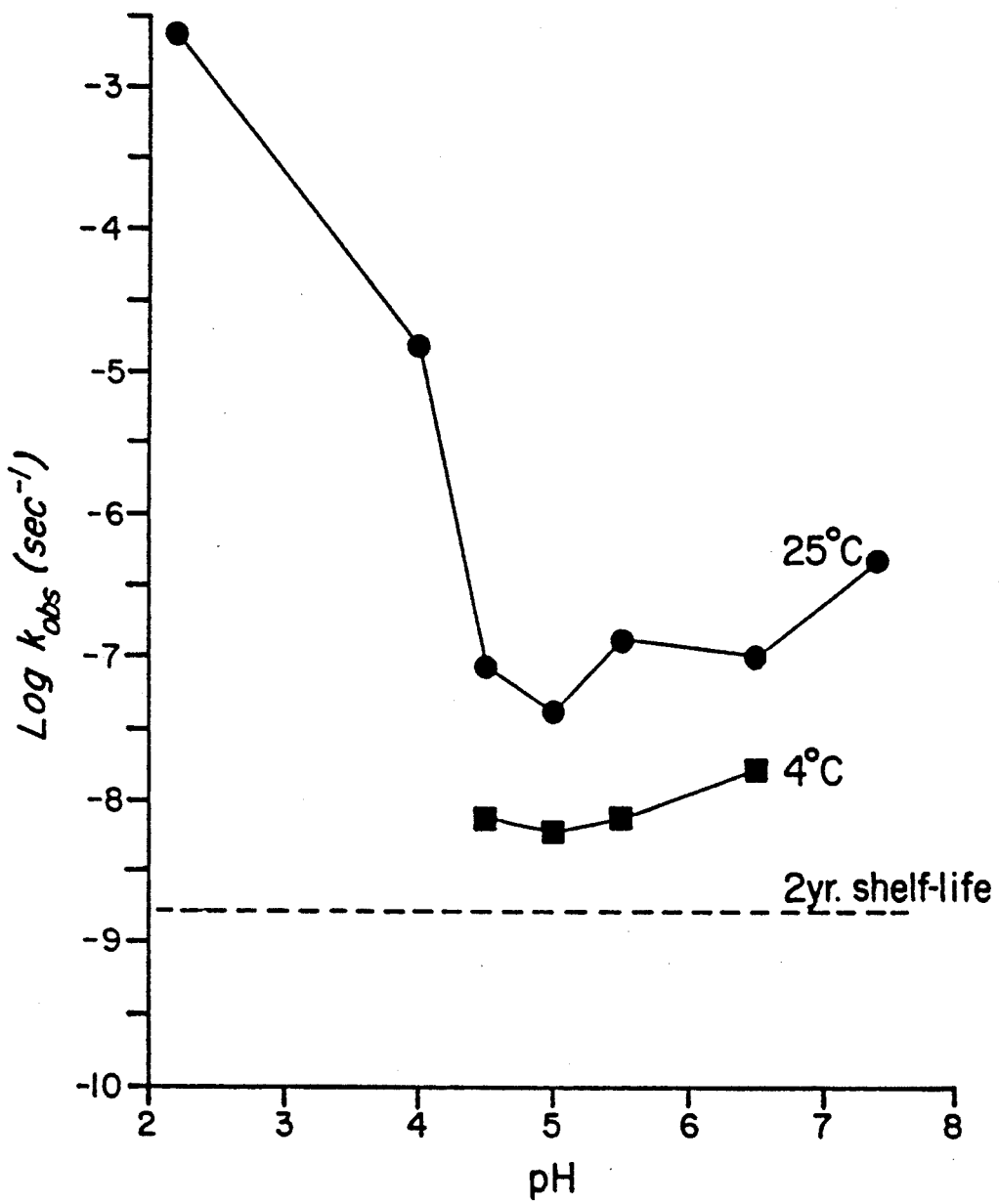
FIG. 5 is a pH vs. logarithm-rate profile obtained from HPLC stability data at 25° C. and 4° C. for 100 ug/ml of reduced bFGF in buffered solutions containing 1 mM calcium disodium EDTA.

Since the present bFGF formulations are intended for therapeutic use with animals, the pH of the formulation must be physiologically acceptable to the animal and not contribute to the destabilization of the growth factor. Generally, the pH of the stabilized bFGF formulation ranges from about 2 to about 8, with a preferred pH range being from about 4.5 to about 6.5, and more preferably about 5.0, as indicated by FIG. 5, which illustrates the effect of pH on stability of bFGF. The pH of the formulation can be adjusted easily by adding effective amounts of a pharmaceutically acceptable buffer or acid to obtain the required pH. While suitable acids and buffers are known to those skilled in the art, the addition of certain buffers, such as citrate or aspartate, offers secondary advantages. Citrate, for example, is pharmaceutically acceptable, with good pH buffering capacity at pH 5, but moreover is a nonvolatile buffer which is very useful for lyophilization processes, and also serves as an auxiliary metal chelator, complementing other stabilizers, such as EDTA and edetate salts, in the freeze-dried final product.

Through utilization of recombinant DNA techniques, a sufficient supply of bFGF can now be manufactured for the repair of traumatized tissue as a result of wounding, surgery, burns, fractures or neurological degeneration. This growth factor is known as a potent mitogen for a wide variety of cell types of mesodermal and neuroectodermal origin. FGF promotes the proliferation of sensitive target cells such as vascular endothelial cell and fibroblasts (Gospodarowicz et al., (1987) *Endocr Rev* 8:95-114; Baird et al. (1986) *Recent Prog Horm Res* 42:143-205), is chemotactic for a variety of cell types (Moscatelli et al., (1986) *Proc Natl Acad Sci U.S.A.* 83:2091-2095; Senior et al., (1986) *Biochem Biophys Res Commun* 141:67-72; Presta et al., (1986) *Mol Cell Biol* 6:4060-4066), and induces the synthesis of collagenase and plasminogen activator in endothelial cells (Moscatelli et al., supra). Basic FGF is angiogenic "in vivo" (Gospodarowicz et al., (1979) *Exp Eye Res* 28:501-514) and has neurotrophic properties (Morrison et al., (1986) *Proc Natl Acad Sci U.S.A.* 83:7537-7541). Exogenously supplied FGF has effects on wound healing (Davidson et al., (1985) *J Cell Bio* 100:1219-1227), bone healing (Canolis et al., (1987) *J Clin Invest* 79:52-58), vascular grafting (Griesler et al., (1986) *Trans Am Soc Artif Intern Organs* 32:346-349), lens regeneration (Yamada (1982) *Cell Biology of the Eye*, McDevitt, D. S., ed., pp. 193-234, Academic Press, New York), and limb regeneration (Gospodarowicz and Mescher, (1981) *Advances in Neurology: Neurofibromatosis*, Riccardi, V. M., and Mulvihill, J. J., eds., Vol. 29, p. 149 Raven Press, New York).

For topical administration, which is the most appropriate with regard to superficial lesions, standard topical formulations are employed using, for example, 0.01-10% of FGF in solution. The concentration of FGF in gel or other formulation depends, of course, on the severity of the wound or stage of disease and the nature of the subject.

As with the topical administration, for sustained-release delivery, the concentration of FGF in the formulation depends on a number of factors, including the severity of the condition. In general, the formulations are constructed so as to achieve a constant local concentration of about 100 times the serum level of factor or 10 times the tissue concentration, as prescribed by Buckley et al., (1985) *Proc Natl Acad Sci* (U.S.A.) 82:7340-7344). Based on an FGF concentration in tissue of 5-50 ng/g wet weight (comparable to EGF at 60 ng/g wet weight), release of 50-5000 ng FGF per hour is acceptable.

The following examples further illustrate the formulation of the invention and a process for its manufacture. These examples are not intended to limit the invention in any manner.

EXAMPLE 1

Expression and Purification of bFGF

Cells of *E. coli* B ATCC strain 23848 transformed with plasmid DNA pTsF-9 delta-betaGAL were cultured under standard conditions to generate the cell mass used below for the purification of bFGF.

Six hundred grams of biomass were suspended in 3.5 liters of 20 mM Tris, pH 7.5, 2 mM EDTA and ruptured by passage through a microfluidizer. Six hundred fifty ml were aliquoted and PMSF was added to 0.1 mM final concentration. The cells were centrifuged at 5000 rpm in a GSA rotor for 10 min. The supernatant was adjusted to 0.6M NaCl and centrifuged at 13000 rpm for 10 min in a GS-3 rotor.

The supernatant was loaded at a flow rate of 2 ml/min onto 40 ml of heparin-Sepharose preequilibrated with 20 mM Tris, pH 7.5, 1 mM EDTA. When loading was completed, the column was washed with the equilibration buffer until baseline absorbance was achieved. The buffer was then changed to 20 mM Tris, pH 7.5, 1 mM EDTA, 1M NaCl and eluted until baseline absorbance was achieved. The column was eluted with a 300 ml linear gradient of 1–3M NaCl in 20 mM Tris pH 7.5, 1 mM EDTA. The bFGF eluted as a broad peak and was collected in one fraction. The protein was passed through DEAE-Sepharose equilibrated in the same buffer as the protein and the flow-through was collected. The sample was concentrated in an Amicon stirred cell using a YM-10 membrane. DTT was added to a final concentration of 25 mM and loaded onto a Sephadex G-100 column (2.5 cm×95 cm) equilibrated in PBS and the column was eluted in the same buffer. The eluate containing protein was collected and loaded onto heparin-Sepharose for a second time. The column had been equilibrated in 20 mM Tris, 0.6M NaCl. After loading was complete, the column was washed with the same buffer and then replaced with 20 mM, Tris pH 7.5, 1M NaCl. After the absorbence returned to baseline, the column was eluted with 20 mM Tris, pH 7.5, 2M NaCl. The protein eluted as a single sharp peak and was labeled 1277-47.

A new alternative to the purification of bFGF by heparin-affinity chromatography is described in co-owned, co-pending U.S. Pat. No. 5,136,025, filed even date herewith, the relevant portions of which are incorporated specifically herein by reference. In this procedure, a novel purification scheme is described which employs copper affinity chromatography.

EXAMPLE 2

Effect of Oxygen and Metal Ions on Reduced FGF

Because proteins with free cysteines may undergo autooxidation catalyzed by metals, studies were carried out to observe the effect of metals on reduced bFGF in solutions in the presence or absence of EDTA.

It has been shown by others that the kinetics of disulfide formation can be measured by monitoring changes in elution position from various HPLC columns (Wu et al., (1983) *Anal Biochem* 129:345-348). One assay for oxidation used in the present examples relies on a shift in elution position on RP-HPLC following oxidation.

A. Initial Experiments Using Lot 1277-47 from Example 1—Effect of Oxygen and Metal Ions A kinetic experiment was conducted to compare the kinetic reaction for destabilization of reduced bFGF at pH 7.4 in phosphate buffer without EDTA at 37° C. under air and after oxygen removal by purging with argon. About 100 ug/ml of reduced bFGF (lot 1277-47 from Example 1) in 50 mM sodium phosphate, pH 7.4 (with ionic strength adjusted to 0.15M with sodium chloride) was prepared and 100 ul aliquots of this reaction mixture were assayed by reverse-phase HPLC at various time periods over a 96 hour period. Analysis by reverse-phase HPLC used a Hewlett Packard 1090M HPLC system, a Vydak 5 um column (4.6×250 mm) with C18-bonded phase (300 angstrom pore-size) and a mobile phase consisting of acetonitrile with 0.1% trifluoroacetic acid (TFA) and water with 0.1% TFA. Using a flow rate of 1 ml/min, a 5–60% acetonitrile gradient (5–60% in 35 min, 60–5% in 5 min) in 0.1% v/v TFA was established.

Rate constants were observed to be similar ($1.18 \times 10^{-5}$ s$^{-1}$ and $1.15 \times 10^{-5}$ s$^{-1}$); however, it was very difficult to remove all available oxygen from solution. (For such low concentrations of bFGF (100 ug/ml or 5 uM bFGF), it is not possible to reduce oxygen levels to uM levels by purging with argon.

In another example, approximately 20 ppm of specific metal ions (ferric chloride, cupric chloride, calcium chloride, and zinc chloride) were added to 100 ug/ml of reduced bFGF at pH 7.4 in phosphate buffer without EDTA at room temperature, under air and also after removal of oxygen by purging with argon. Each sample was assayed within moments after the introduction of the respective metal ions by reverse-phase HPLC. Results by reverse-phase HPLC showed complete conversion of the principal peak to a broader peak with shorter retention time in the presence of each metal ion. Although complete conversion occurred in both the argon-saturated sample and the air-saturated sample, the resultant peak was much sharper in the sample which had reduced oxygen. Conversion was immediate after mixing of metal ions and protein solutions. This observation indicates that the amount of oxygen in solution is one factor affecting stability of bFGF solutions containing metal ions.

B. Experiments Using FG001 (Cu$^{+1}$-Affinity Purified Material)

In this example, 100 ul of bFGF (approximately 10 ug/ml), which had been purified as described in co-pending U.S. Pat. No. 5,136,025 and designated FG001, was analyzed by heparin-affinity HPLC using a Hewlett Packard 1090L HPLC system, a 7.5×75 mm heparin-TSD column (Bio-Rad or Toso-Haas) and a mobile phase consisting of buffer A (20 mM Tris, pH 7.5, with 3M NaCl) and buffer B (20 mM Tris, pH 7.5). At a flow rate of 1 ml/min, a 24–100% gradient was established (24–40 A in 1 min, 40–100% A in 23 min, 100% A in % min, and 100–24% A in 5 min).

By reversed-phase or heparin-affinity HPLC, samples of reduced FG001 spiked with cupric chloride (0.45 to 6 mM Cu$^{+2}$ ion) showed rapid loss of the main peak at pH 5.0 in acetate buffer, with reversed-phase HPLC analyses showing conversion of the main peak to a peak with shorter retention time. Analysis by reverse-phase HPLC used a Hewlett Packard 1090M HPLC system, a Vydak 5 um column (4.6×250 mm) with C18-bonded phase (300 angstrom pore-size) and a mobile phase consisting of acetonitrile with 0.1% trifluoroacetic acid (TFA) and water with 0.1% TFA. Using a flow rate of 1 ml/min, a 5–60% acetonitrile gradient (5–60% in 35 min, 60–5% in 5 min) in 0.1% v/v TFA was established.

Figure 1B:
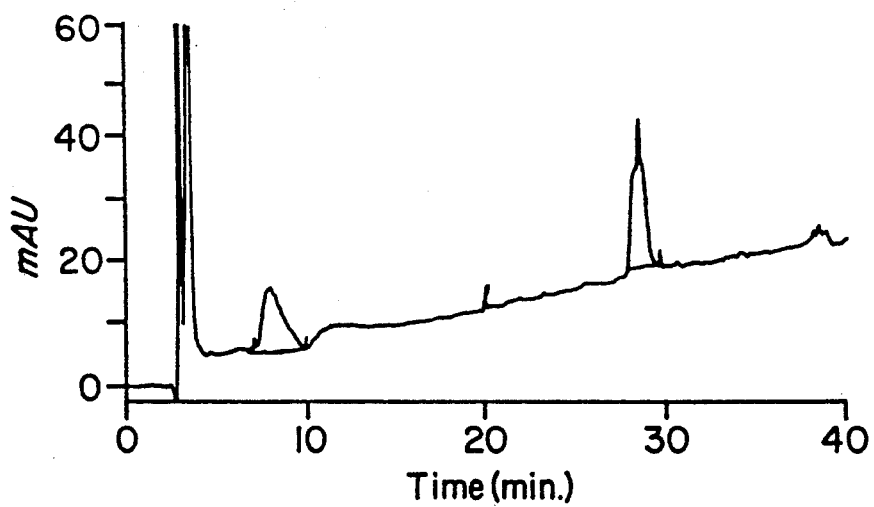
Figure 2A:
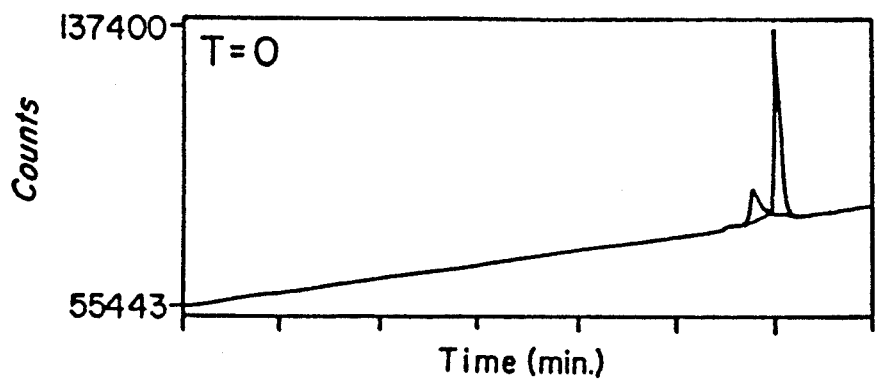
FIGS. 2A-2D show reverse-phase HPLC chromatograms of bFGF prepared in the presence of EDTA, stored at 25° C. at pH 5.0, as a function of time.
Figure 2B:
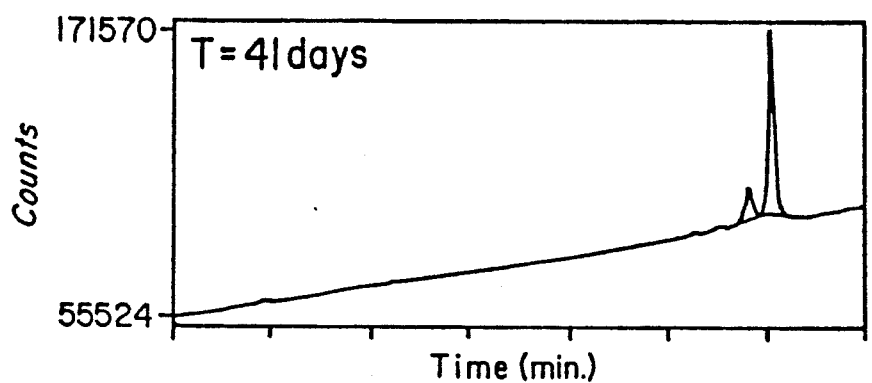
Figure 2C:
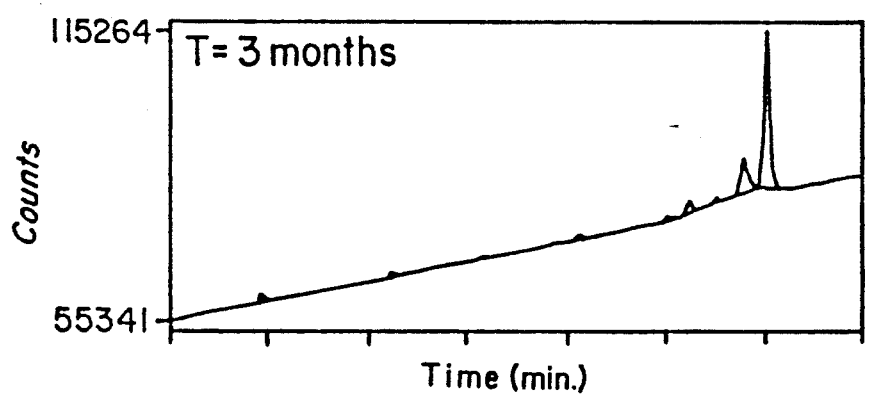
Figure 2D:
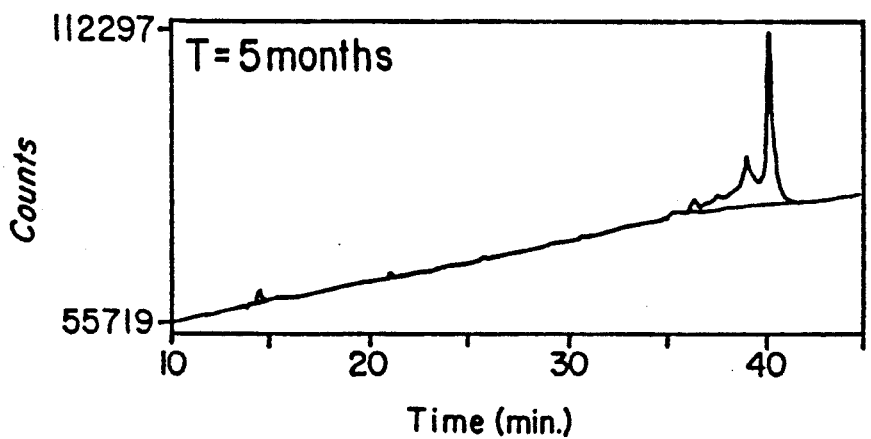

In contrast, the presence of EDTA prevented the conversion of bFGF observed after spiking with cupric ions. Comparison of the chromatograms showed that bFGF solutions (100 ug/ml) containing 1 mM EDTA showed no chromatographic changes after spiking with cupric chloride up to 0.45 mM cupric ion or 28 ppm (FIG. 1A), while FIG. 1B showed the conversion of the main peak to a peak with shorter retention time in the absence of EDTA. The major peak eluting at 30 min in FIG. 1A is believed to represent reduced bFGF; the faster eluting peak at 28 min in FIG. 1B is believed to represent oxidized and/or aggregated forms.

Higher cupric ion concentrations (0.9 mM or 57 ppm) added to bFGF solutions containing EDTA resulted in partial conversion to a form with shorter retention on RP-HPLC. A concentration of 95 ppm-spiked cupric ion resulted in complete conversion, with or without EDTA present. The effects of extremely high concentrations of cupric ions were investigated for research purposes only as commercial bFGF formulations for therapeutic indications would not be exposed to such high metal ion concentrations.

Size exclusion chromatography (SEC) using a Pharmacia Superose 12 size exclusion column with mobile phase consisting of 20 mM sodium phosphate buffer, pH 6.5, with 1.0M NaCl with flow rate of 0.5 ml/min was employed to evaluate bFGF samples spiked with cupric chloride under oxidizing conditions (i.e., without EDTA). Samples of bFGF (100 ug/ml) in 50 mM sodium acetate (pH 5.0) or Tris buffer (pH 7.4) with ionic strength of 0.15M (adjusted by addition of sodium chloride) were spiked with 0.9 mM cupric chloride. Approximately 10 ug of bFGF (100 ul injection) were assayed by SEC. With spiked cupric ion at pH 5.0, a higher molecular weight form (likely a dimer) was observed. However, at pH 7.4 with spiked cupric ion, no bFGF monomer or higher molecular weight bFGF peaks were observed by SEC, indicating that high molecular weight multimers could be sticking to the SEC column, inasmuch as oxidation of cysteine residues is more favored at pH 7.4 than at pH 5.0 (owing to the $pK_a$ of the cysteine moiety).

EXAMPLE 3

Early Stability Studies of bFGF

A. Reaction Rates with and without EDTA

Figure 3A:
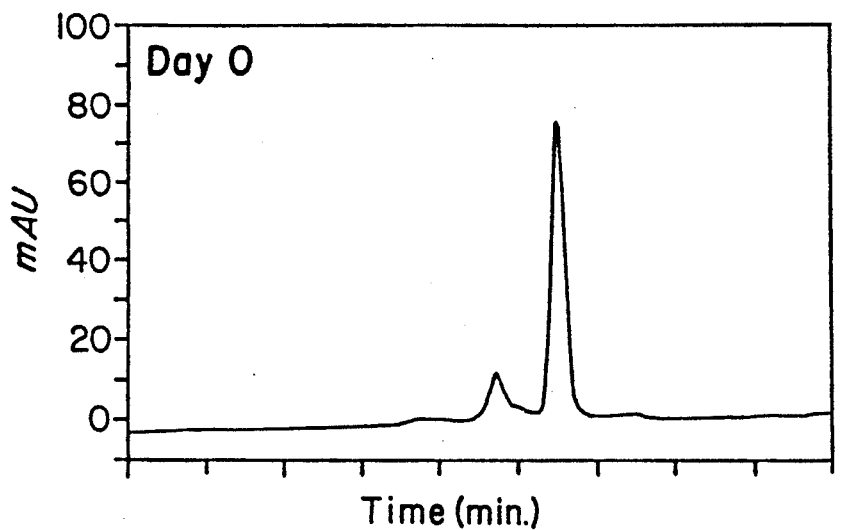
FIGS. 3A-3C show reverse-phase HPLC chromatograms of bFGF prepared in the absence of EDTA stored at 25° C. at pH 5.0, as a function of time.
Figure 3B:
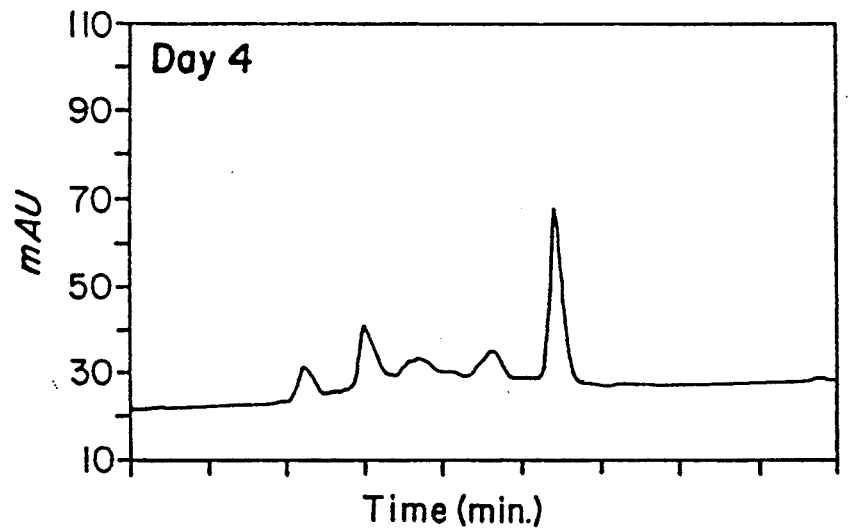
Figure 3C:
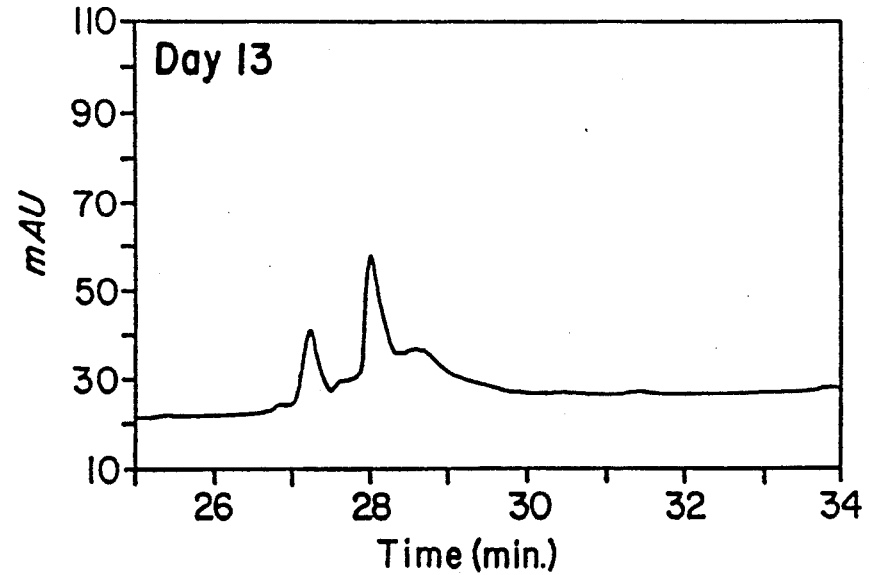

The half-life, determined by reverse-phase HPLC, of 100 ug/ml bFGF in phosphate (pH 7.4) or acetate buffer (pH 5.0) at 25° C. was determined to be about 14 hours at pH 7.4 and 4 days at pH 5.0 in the absence of EDTA. In contrast, when EDTA was present, the half-life of the protein was about 18 days at pH 7.4 and 3 to 4 months at pH 5.0. In light of these results, samples were prepared, aged and analyzed by reverse-phase HPLC to determine the long-term stability of the samples in the presence or absence of EDTA at pH 5.0. The chromatograms shown in FIGS. 2A-2D prepared from samples with 1 mM calcium disodium EDTA showed that the main peak is still present after 5 months at 25° C., although some decomposition occurred (as taught above except that a 5-40% in 35 min, 40-5% in 5 min gradient was substituted). Analysis by reverse-phase HPLC used a Hewlett Packard 1090M HPLC system, a Vydak 5 um column (4.6×250 mm) with C18-bonded phase (300 angstrom pore-size) and a mobile phase consisting of acetonitrile with 0.1% trifluoroacetic acid (TFA) and water with 0.1% TFA. Using a flow rate of 1 ml/min, a 5-60% acetonitrile gradient (5-60% in 35 min, 60-5% in 5 min) in 0.1% v/v TFA was established. As shown in FIGS. 3A-3C, the main peak disappeared after 13 days storage at 25° C. in the absence of EDTA to yield a complex mixture, HPLC performed as shown under conditions shown above in Example 2B.

B. Stability at Acidic pH with and without EDTA

The half-life, determined by heparin-affinity HPLC, of 100 ug/ml reduced bFGF in acetate buffer at pH 4.0, was about 15 minutes at 25° C. without EDTA, in contrast to 12 hours with EDTA present. At pH 2.2, in glycine buffer, 100 ug/ml reduced bFGF showed only 12% remaining by heparin-affinity HPLC after 15 minutes at 25° C.

C. Effect of EDTA Concentration and EDTA Salt

A one-month stability study was carried out using buffered solutions of bFGF at pH 7.4 and pH 5.0 with either 0.1 mM disodium EDTA or 1.0 mM disodium EDTA, and 1.0 mM calcium disodium-EDTA (pH 7.4). The protein was fully bioactive after one month's storage in each salt at all pH ranges. HPLC results indicated that both concentrations of the edetate salts, 0.1 mM and 1.0 mM, were equally effective, showing stability for one month at pH 5.0. However, the higher EDTA concentration affords better protection against effects of trace metal ions, with 28 ppm cupric ions showing no effect on reduced bFGF when 1 mM EDTA is present. HPLC results showed bFGF was stable for at least 1 month at pH 5.0 at 25° C. and for more than 5 months at 4° C. (Table 1), but physical changes were observed at pH 7.4 (data not shown).

TABLE 1

Stability Data
100 ug/ml reduced bFGF in 50 mM sodium acetate with ionic strength adjusted to 0.15 M with sodium chloride and containing 1 mM disodium EDTA, pH 5.0.

| Temperature °C. | Time (day) | % bFGF main peak remaining by | |
|---|---|---|---|
| | | RP-HPLC* | Heparin-HPLC |
| 25 | 0 | 100 | 100 |
| | 3 | 107 | |
| | 4 | 108 | |
| | 8 | 109 | |
| | 13 | 106 | |
| | 25 | 99 | 98 |
| | 33 | 84 | 83 |
| 4 | 0 | 100 | 100 |
| | 3 | 98 | |
| | 8 | 100 | |
| | 30 | 102 | 98 |
| −20 | 0 | 100 | 100 |
| | 8 | 102 | |
| | 25 | 101 | 100 |
| | 30 | 101 | 100 |
| | 33 | 101 | |

*See HPLC conditions in Example 2B.

D. Comparison of Different Salts

No difference was observed kinetically between 1.0 mM disodium EDTA and 1.0 mM calcium disodium EDTA. However, early in vivo wound-healing studies showed a biological difference between calcium disodium EDTA and disodium EDTA, reflecting better healing with the calcium salt. Later in vivo work has not shown a difference.

E. Bioassay Results

FGF formulations were tested in a baby hamster kidney-21 (BHK) microtiter cell proliferation assay. This assay is a modification of published procedures for the measurement of bFGF potency using BHK-21 cells (Gospodarowicz and Cheng, *J Cell Physiol* (1986) 128:475-484 and Neufeld et al., *Reg Peptides* (1986) 13:293-305). This assay differs from previously described assays in that the entire assay is performed in microtiter tissue culture plates and the extent of cell proliferation is determined colorimetrically after fixing the cells with glutaraldehyde and staining cell proteins with crystal violet.

On the first day of the assay, serum-free medium supplemented with insulin and transferrin is dispensed into 96-well tissue culture plates, and a bFGF standard or samples of unknown activity are added to quadruplicate wells and serially diluted. Following serial dilution of the bFGF, the indicator cells (BHK-21 cells) are added to all wells and the microtiter plates are returned to an incubator at 37° C. for 72 hours. The extent of cell proliferation is determined by fixing the cells to the culture plates with glutaraldehyde and staining the cells with crystal violet. The extent of cell proliferation in each well is then determined by scanning the plate with an ELISA plate reader.

Figure 4A:
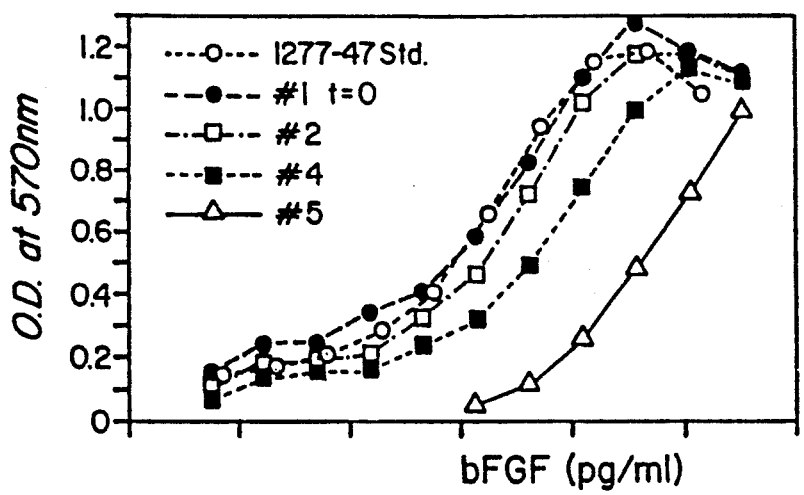
FIGS. 4A-4C show bioassay results from bFGF samples stored at pH 5.0 at 25° C. with a) no EDTA; b) 0.1 mM disodium EDTA and c) 1 mM disodium EDTA.
Figure 4B:
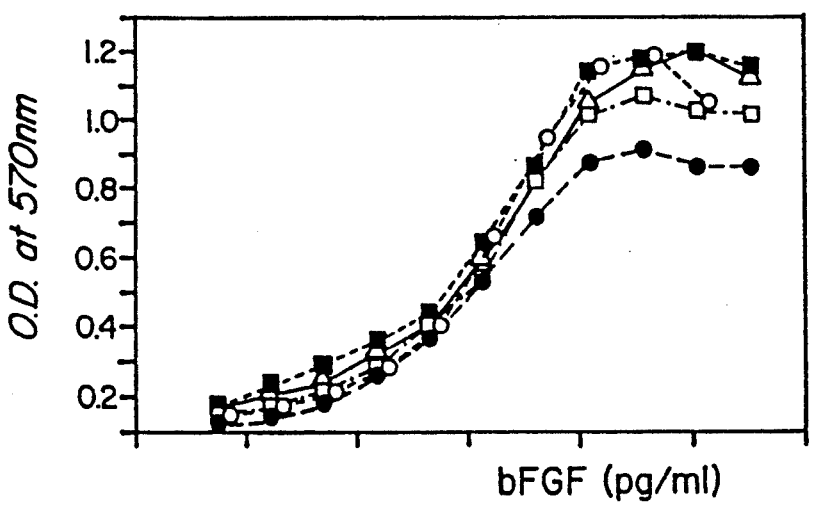
Figure 4C:
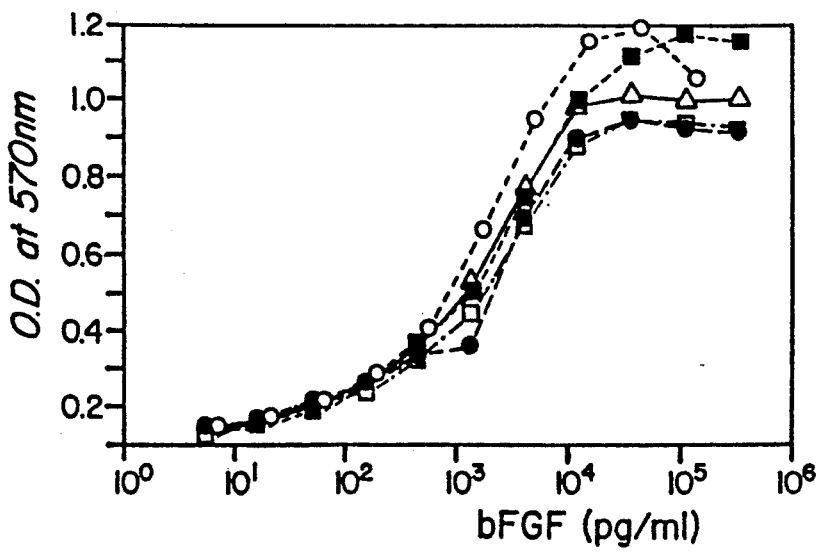

Cell culture bioassay showed a clear advantage in use of EDTA to stabilize bFGF as compared with bFGF in the absence of EDTA. FIG. 4 shows bioassay results from samples stored at pH 5.0 at 25° C. with a) no EDTA, b) 0.1 mM disodium EDTA, and c) 1.0 mM disodium EDTA. A shift in the curve to the right reflects loss of activity. FIG. 4A, showed a progressive loss of activity with storage without EDTA while both 0.1 mM (FIG. 4B) and 1.0 mM EDTA (FIG. 4C) showed protection.

EXAMPLE 4

Long-Term Stability Study

Preformulation studies were carried out to define formulation conditions for reduced bFGF which would stabilize the protein both biologically and physically. Solution stability of bFGF (100 ug/ml) was evaluated at 25° C. in aqueous buffers (50 mM) at 0.15M ionic strength (adjusted by addition of sodium chloride) at pH 5.0 and pH 7.4, with and without EDTA present as stabilizer. Stability data obtained from reversed-phase HPLC assay of pH 5.0 samples of reduced bFGF aged at 25° C., with and without EDTA, were plotted as percent initial (based on peak area of the main peak) versus time. These HPLC data showed that stability of bFGF solutions without EDTA was poor, with half-lives at 25° C. of 14 hours and 4 days, respectively, in phosphate buffer at pH 7.4 and in acetate buffer at pH 5.0. In contrast, the presence of EDTA (0.1 mM and 1.0 mM) greatly increased the stability of bFGF; for example, a half-life of 103 days at 25° C. in the presence of 1 mM EDTA was obtained.

Samples were then prepared over a pH range from pH 2.2 to pH 7.4 to generate a pH rate profile at 25° C. at 100 ug/ml bFGF in 50 mM aqueous buffers (glycine at pH 2.2 and 3.2; sodium acetate at pH 4.0, 4.5, and 5.0; and sodium phosphate at pH 6.5 and 7.4) containing 1 mM calcium disodium EDTA with ionic strength adjusted to 0.15M with sodium chloride. Stability of aged samples (at least 6 timepoints) was followed for approximately three half-lives at 25° C. Samples were assayed by heparin-affinity HPLC. Reaction rates were obtained from a first-order fit of the data or from initial rates when the data did not fit first order kinetics for more than one half-life. The pH of each batch was plotted as a function of the logarithm of the observed reaction rate, $k_{obs}$, to construct a pH-rate profile for bFGF in solution. As shown in FIG. 5, samples showed the best stability from pH 4.5 to pH 5.0 to pH 6.5, with the pH of maximum stability at approximately pH 5.0 at 25° C.

Stability data for the FGF formulation are tabulated in Table 2 showing the results at pH 5.0 as a function of temperature. Table 3 shows a more complete set of data for pH 5.0 at 4° C., the preferred storage condition for the solution formulation. The biological activity of the bFGF formulation was tested in an adrenal cortex capillary endothelial (ACE) cell proliferation assay as described by Gospodarowicz et al. (*J Cell Physiol* (1985) 122:323-332). Briefly, approximately $1 \times 10^4$ cells were plated in 2 ml of DME 16 supplemented with 10% calf serum, 50 units/well of penicillin and 50 units/well of streptomycin in a Falcon 6-well plate. Appropriate dilutions (1 pg/ml to 1 ug/ml final concentration) of each sample, as well as wild-type (bovine pituitary basic) FGF were added in 10 ul volumes to the cells. As a negative control, 6 wells without added FGF samples were run simultaneously. The plates were incubated at 37° C. for 48 hours and cell samples were re-added to the appropriate well and incubated for an additional 48 hours at 37° C. Cells were then trypsinized, collected and counted in a Coulter counter.

TABLE 2

| Storage Time | Stability Data by Reversed-Phase HPLC[a] | | |
|---|---|---|---|
| | % bFGF Remaining[b] | | |
| (days) | 25° C. | 4° C. | −20° C. |
| 0 | 100.0 | 100.0 | 100.0 |
| 4 | 106.0 | 99.6 | 97.0 |
| 14 | 103.5 | 102.0 | 103.1 |
| 16 | 102.0 | 109.9 | 104.2 |
| 17 | 91.5 | 104.9 | 103.9 |
| 19 | 96.3 | 102.3 | 104.9 |
| 33 | 88.1 | 102.3 | 102.0 |
| 41 | 85.5 | 102.0 | 109.8 |
| 61 | | 101.6 | 105.7 |
| 93 | 58.5 | 99.8 | 102.1 |
| 125 | 54.1 | 95.8 | 93.4 |
| 156 | 45.7 | 95.2 | 93.4 |
| 190 | 10.3 | | |

[a]Solution contains 100 ug/ml bFGF in 50 mM sodium acetate, pH 5.0 with 1 mM calcium disodium EDTA with isotonicity adjusted by addition of sodium chloride.
[b]Percent initial.

TABLE 3

Stability Data by Heparin-Affinity HPLC, Reversed-Phase HPLC, bFGF[a] in Polypropylene Containers at 4° C.

| Storage Time (Days) | % bFGF Remaining[b] | |
|---|---|---|
| | Heparin-TSK HPLC | Reversed-Phase HPLC |
| 0 | 100.0 | 100.0 |
| 4 | 95.2 | 99.6 |
| 9 | 97.8 | |
| 14 | 98.7 | 102.0 |
| 16 | 97.4 | 109.9 |
| 17 | 103.7 | 104.9 |
| 19 | 96.9 | 102.3 |
| 33 | 102.6 | 102.3 |
| 41 | 104.4 | 102.0 |
| 61 | 105.2 | 101.6 |
| 93 | 97.1 | 99.8 |
| 125 | 88.4 | 95.8 |
| 156 | 96.0 | 95.2 |

TABLE 3-continued

Stability Data by Heparin-Affinity HPLC, Reversed-Phase HPLC, bFGF[a] in Polypropylene Containers at 4° C.

| Storage Time (Days) | % bFGF Remaining[b] | |
|---|---|---|
| | Heparin-TSK HPLC | Reversed-Phase HPLC |
| 190 | 90.4 | |

[a]Solution contains 50 mM sodium acetate, pH 5.0, with 1 mM calcium disodium EDTA with isotonicity adjusted by addition of sodium chloride.
[b]Percent initial based on main peak area for HPLC methods.

Samples were also stored at 4° C. and −20° C. at pH 4.5, 5.0, 5.5 and 6.5 for six months, but rate constants could not be accurately determined because no more than 30% degradation was observed by HPLC over the six-month time period. At pH 5.0, no more than 10% degradation was observed by HPLC after six months of storage.

From these findings, the condition chosen for the solution formulation of bFGF was stored at 4° C. in 50 mM sodium acetate buffer, pH 5.0, with 1 mM calcium disodium EDTA, with isotonicity adjusted by addition of sodium chloride.

EXAMPLE 5

Stabilization of bFGF Using Citrate

This experiment was carried out using 100 ug/ml reduced bFGF in 50 mM citrate solution, pH 5.0, at 0.15M ionic strength adjusted with sodium chloride. Samples were aged in Sarstedt polypropylene tubes at controlled temperature. Initial control samples were stored at −80° C. At 33 day timepoint, a sample was pulled for assay; 100 ul of sample and the initial control sample were injected onto a reverse-phase HPLC column without further dilution. Values recorded were percent initial.

The stability of bFGF in citrate solution was slightly less than found previously with acetate solution and EDTA (82% remaining after 33 days at 25° C. for citrate versus 88% remaining by the same reversed-phase HPLC method for the acetate/EDTA solution).

EXAMPLE 6

Lyophilization Experiments

In one experiment, 10 mg/ml of bulk bFGF were diluted to 500 ug/ml in 10 ml glycine, pH 5.0, with 10 mM calcium disodium EDTA. A 2 ml sample was lyophilized and then reconstituted using 10 ml purified water. In a second experiment, 10 mg/ml bulk bFGF were diluted to 500 ug/ml in 20 mg/ml mannitol, 20 mM sodium acetate, pH 5.0, with 10 mM EDTA. A 2 ml sample was lyophilized and then reconstituted using 10 ml purified water. Each of the lyophilized, resuspended bFGF samples were subjected to heparin-HPLC analysis. Complete recovery by peak area was observed for the lyophilized samples, and the samples were shown to be biologically active by cell culture bioassay.

It is noted that these formulations are not ideal because vacuum pressure removes acetate during the freeze-drying process. A preferred buffer to overcome this problem employs citrate and other nonvolatile carboxylate buffers, along with bulking agents such as, for example, mannitol, lactose, trehalose, glycine, glycylglycine, glucose, sucrose, polyvinylpyrrolidone, glutamate, galactose, and alginate, maltatriose and other oligomeric sugars.

Modification of the above-described modes for carrying out the invention that are obvious to those of skill in pharmaceutical formulation or related fields are intended to be within the scope of the following claims.

We claim:

1. A stabilized basic fibroblast growth factor pharmaceutical formulation consisting essentially of a basic fibroblast growth factor (bFGF) and a chelating agent or a pharmaceutically acceptable salt thereof in an amount effective to stabilize said bFGF.

2. The stabilized bFGF formulation of claim 1 wherein the chelating agent is an aminopolycarboxylic acid.

3. The stabilized bFGF formulation of claim 1 wherein the chelating agent is selected from the group consisting of ethylenediaminetetraacetic acid (EDTA), diethylenetriaminepentaacetic acid (DTPA), nitrilotriacetic acid (NTA), glutamic acid, and aspartic acid.

4. The stabilized bFGF formulation of claim 3 wherein the chelating agent is EDTA.

5. The stabilized bFGF formulation of claim 3 wherein the chelating agent is DTPA.

6. The stabilized bFGF formulation of claim 1 wherein the pH range of the formulation is from about 4.5 to about 8.

7. The stabilized bFGF formulation of claim 6 wherein the pH range of the formulation is about 4.5–6.5.

8. The stabilized bFGF formulation of claim 1 wherein the pharmaceutically acceptable salts are a group consisting of the salts of sodium, potassium and calcium ions.

9. The stabilized bFGF formulation of claim 1 wherein said chelating agent has a binding strength for copper ion of about 7 to 15.

10. The stabilized bFGF formulation of claim 9 wherein said chelating agent has a binding strength for copper ion of about 10 to 15.

11. The stabilized bFGF formulation of claim 10 wherein said chelating agent has a binding strength for copper ion of about 15.

12. The stabilized bFGF formulation of claim 1 wherein said basic fibroblast growth factor is from a mammalian source.

13. The stabilized bFGF formulation of claim 10 which is human basic fibroblast growth factor.

14. The stabilized bFGF formulation of claim 1 wherein said basic fibroblast growth factor is a recombinant protein.

15. The stabilized bFGF formulation of claim 1 wherein said formulation is in a dry state.

16. The stabilized bFGF formulation of claim 1 wherein said formulation is dispersed in an aqueous solution.

17. The stabilized bFGF formulation of claim 13 wherein said formulation is dissolved in an aqueous solution.

18. The stabilized bFGF formulation of claim 1 which is formulated as a controlled, continuous release formulation.

19. The stabilized bFGF formulation of claim 14 wherein said chelating agent is present in amounts of from about 0.001 to about 2.0 percent by weight of the stabilized fibroblast growth factor formulation.

20. The stabilized bFGF formulation of claim 13 wherein said chelating agent is present in amounts of from about 0.01 to about 40 percent by weight of the stabilized fibroblast growth factor formulation.

* * * * *